United States Patent

Castro Pineiro

[11] Patent Number: 6,051,572
[45] Date of Patent: Apr. 18, 2000

[54] AZETIDINE, PYRROLIDINE AND PIPERIDINE DERIVATIVES

[75] Inventor: Jose Luis Castro Pineiro, Bishops Stortford, United Kingdom

[73] Assignee: Merck Sharp & Dohme Ltd., Hoddesdon, United Kingdom

[21] Appl. No.: 09/068,066

[22] PCT Filed: Oct. 28, 1996

[86] PCT No.: PCT/GB96/02625

§ 371 Date: Apr. 28, 1998

§ 102(e) Date: Apr. 28, 1998

[87] PCT Pub. No.: WO97/16445

PCT Pub. Date: May 9, 1997

[30] Foreign Application Priority Data

Nov. 1, 1995 [GB] United Kingdom ............... 9522372

[51] Int. Cl.⁷ ............... C07D 401/14; C07D 403/14; A61K 31/445

[52] U.S. Cl. ............... 514/235.2; 514/232.8; 514/234.2; 514/234.5; 514/235.8; 514/236.2; 514/252; 514/253; 514/255; 514/299; 514/300; 514/301; 514/302; 514/303; 514/322; 514/324; 514/326; 514/362; 514/363; 514/364; 514/373; 514/379; 514/381; 514/383; 514/387; 544/129; 544/134; 544/138; 544/139; 544/140; 544/143; 544/364; 544/367; 544/369; 544/370; 544/371; 544/373; 546/199; 548/127; 548/128; 548/131; 548/134; 548/136; 548/143; 548/207; 548/181; 548/206; 548/241; 548/250; 548/255; 548/266.4; 548/266.6; 548/306.4

[58] Field of Search ............... 514/232.8, 234.2, 514/234.5, 235.5, 235.8, 235.2, 236.5, 236.8, 255, 299, 322, 300, 383; 544/143, 364, 129, 134, 138, 139, 140, 367, 369, 370, 371, 373; 548/266.4, 266.6; 546/199

[56] References Cited

U.S. PATENT DOCUMENTS 5,849,746  12/1998  Chambers et al. .............. 514/253

FOREIGN PATENT DOCUMENTS

94/02477  2/1994  WIPO .
95/32196  11/1995  WIPO .
96/04274  2/1996  WIPO .
96/16056  5/1996  WIPO .

Primary Examiner—Mukund J. Shah
Assistant Examiner—Deepak R. Rao
Attorney, Agent, or Firm—James L. McGinnis; David L. Rose

[57] ABSTRACT

A class of azetidine, pyrrolidine and piperidine derivatives, substituted by inter alia a phenylmorpholinyl, phenylpiperidinyl or benzimidazolone moiety, are selective agonists of 5-$HT_1$-like receptors, being potent agonists of the human 5-$HT_{1D\alpha}$ receptor subtype whilst possessing at least a 10-fold selective affinity for the 5-$HT_{1D\alpha}$ receptor subtype relative to the 5-$HT_{1D\beta}$ subtype; they are therefore useful in the treatment and/or prevention of clinical conditions, in particular migraine and associated disorders, for which a subtype-selective agonist of 5-$HT_{1D}$ receptors is indicated, whilst eliciting fewer side-effects, notably adverse cardiovascular events, than those associated with non-subtype-selective 5-$HT_{1D}$ receptor agonists.

8 Claims, No Drawings

AZETIDINE, PYRROLIDINE AND PIPERIDINE DERIVATIVES

This application is a 371 of PCT/GB96/02625 filed Oct. 28, 1996.

The present invention relates to a class of substituted azetidine, pyrrolidine and piperidine derivatives which act on 5-hydroxytryptamine (5-HT) receptors, being selective agonists of so-called "5-HT$_1$-like" receptors. They are therefore useful in the treatment of clinical conditions for which a selective agonist of these receptors is indicated.

It has been known for some time that 5-HT$_1$-like receptor agonists which exhibit selective vasoconstrictor activity are of use in the treatment of migraine (see, for example, A. Doenicke et al., *The Lancet*, 1988, Vol. 1, 1309–11; and W. Feniuk and P. P. A. Humphrey, *Drug Development Research*, 1992, 26, 235–240).

The human 5-HT$_1$-like or 5-HT$_{1D}$ receptor has recently been shown by molecular cloning techniques to exist in two distinct subtypes. These subtypes have been termed 5-HT$_{1D_\alpha}$ (or 5-HT$_{1D-1}$) and 5-HT$_{1D_\beta}$ (or 5-HT$_{1D-2}$), and their amino acid sequences are disclosed and claimed in WO-A-91/17174.

The 5-HT$_{1D_\alpha}$ receptor subtype in humans is believed to reside on sensory terminals in the dura mater. Stimulation of the 5-HT$_{1D_\alpha}$ subtype inhibits the release of inflammatory neuropeptides which are thought to contribute to the headache pain of migraine. The human 5-HT$_{1D_\beta}$ receptor subtype, meanwhile, is located predominantly on the blood vessels and in the brain, and hence may play a part in mediating constriction of cerebral and coronary arteries, as well as CNS effects.

Administration of the prototypical 5-HT$_{1D}$ agonist sumatriptan (GR43175) to humans is known to give rise at therapeutic doses to certain adverse cardiovascular events (see, for example, F. Willett et al., *Br. Med. J.*, 1992, 304, 1415; J. P. Ottervanger et al., *The Lancet*, 1993, 341, 861–2; and D. N. Bateman, *The Lancet*, 1993, 341, 221–4). Since sumatriptan barely discriminates between the human 5-HT$_{1D_\alpha}$ and 5-HT$_{1D_\beta}$ receptor subtypes (cf. WO-A-91/17174. Table 1), and since it is the blood vessels with which the 5-HT$_{1D_\beta}$ subtype is most closely associated, it is believed that the cardiovascular side-effects observed with sumatriptan can be attributed to stimulation of the 5-HT$_{1D_\beta}$ receptor subtype. It is accordingly considered (cf G. W. Rebeck et al., *Proc. Natl. Acad. Sci. USA*, 1994, 91, 3666–9) that compounds which can interact selectively with the 5-HT$_{1D_\alpha}$ receptor subtype, whilst having a less pronounced action at the 5-HT$_{1D_\beta}$ subtype, might be free from, or at any rate less prone to, the undesirable cardiovascular and other side-effects associated with non-subtype-selective 5-HT$_{1D}$ receptor agonists, whilst at the same time maintaining a beneficial level of anti-migraine activity.

The compounds of the present invention, being selective 5-HT$_1$-like receptor agonists, are accordingly of benefit in the treatment of migraine and associated conditions, e.g. cluster headache, chronic paroxysmal hemicrania, headache associated with vascular disorders, tension headache and paediatric migraine. In particular, the compounds according to this invention are potent agonists of the human 5-HT$_{1D_\alpha}$ receptor subtype. Moreover, the compounds in accordance with this invention have been found to possess at least a 10-fold selective affinity for the 5-HT$_{1D_\alpha}$ receptor subtype relative to the 5-HT$_{1D_\beta}$ subtype, and they can therefore be expected to manifest fewer side-effects than those associated with non-subtype-selective 5-HT$_{1D}$ receptor agonists.

Several distinct classes of substituted five-membered heteroaromatic compounds are described in published European patent applications 0438230, 0494774 and 0497512, and published International patent applications 93/18029, 94/02477 and 94/03446. The compounds described therein are stated to be agonists of 5-HT$_1$-like receptors, and accordingly to be of particular use in the treatment of migraine and associated conditions. None of these publications, however, discloses nor even suggests the substituted azetidine, pyrrolidine and piperidine derivatives provided by the present invention.

Moreover nowhere in the prior art mentioned above is there any disclosure of a subtype-selective 5-HT$_{1D}$ receptor agonist having a 5-HT$_{1D_\alpha}$ receptor binding affinity (IC$_{50}$) below 100 nM and at least a 10-fold selective affinity for the 5-HT$_{1D_\alpha}$ receptor subtype relative to the 5-HT$_{1D_\beta}$ subtype.

The compounds according to the present invention are subtype-selective 5-HT$_{1D}$ receptor agonists having a human 5-HT$_{1D_\alpha}$ receptor binding affinity (IC$_{50}$) below 100 nM, typically below 50 nM, suitably below 10 nM and preferably below 1 nM; and at least a 10-fold selective affinity, typically at least a 50-fold selective affinity and preferably at least a 100-fold selective affinity, for the human 5-HT$_{1D_\alpha}$ receptor subtype relative to the 5-HT$_{1D_\beta}$ subtype.

The present invention provides a compound of formula I, or a salt or prodrug thereof:

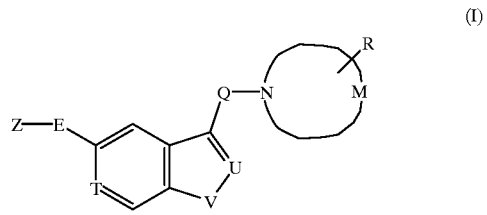

(I)

wherein

Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole;

E represents a chemical bond or a straight or branched alkylene chain containing from 1 to 4 carbon atoms;

Q represents a straight or branched alkylene chain containing from 1 to 4 carbon atoms, optionally substituted in any position by a hydroxy group;

T represents nitrogen or CH;

U represents nitrogen or C—R$^2$;

V represents oxygen, sulphur or N—R$^3$;

R$^2$ and R$^3$ independently represent hydrogen or C$_{1-6}$ alkyl;

M represents the residue of an azetidine, pyrrolidine or piperidine ring;

R represents a group of formula —W—R$^1$;

W represents a chemical bond or a straight or branched alkylene chain containing from 1 to 4 carbon atoms; and $R^1$ represents a group of formula (a), (b), (c) or (d):

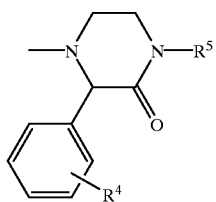
(a)

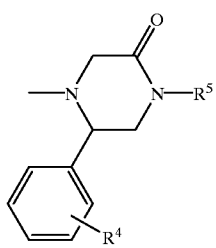
(b)

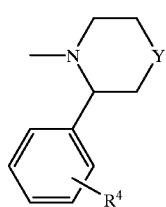
(c)

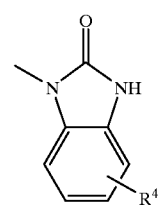
(d)

in which

Y represents oxygen or N—$R^5$;

$R^4$ represents hydrogen, halogen, cyano, nitro, trifluoromethyl, $C_{1-6}$ alkyl, hydroxy, $C_{1-6}$ alkoxy, $C_{2-6}$ alkylcarbonyl, amino, $C_{1-6}$ alkylamino, di($C_{1-6}$) alkylamino, $C_{2-6}$ alkylcarbonylamino, $C_{1-6}$ alkylsulphonylamino or $C_{1-6}$ alkylaminosulphonylmethyl; and $R^5$ represents hydrogen or $C_{1-6}$ alkyl.

The five-membered heteroaromatic ring Z in the compounds of formula I above may be optionally substituted by one or, where possible, two substituents. As will be appreciated, where Z represents an oxadiazole, thiadiazole or tetrazole ring, only one substituent will be possible; otherwise, one or two optional substituents may be accommodated around the five-membered heteroaromatic ring Z. Examples of suitable substituents on the five-membered heteroaromatic ring Z include $C_{1-6}$ alkyl, $C_{2-6}$ alkenyl, $C_{2-6}$ alkynyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, amino, $C_{1-6}$ alkylamino, di($C_{1-6}$) alkylamino, halogen, cyano or trifluoromethyl.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl and tert-butyl. Derived expressions such as "$C_{1-6}$ alkoxy", "$C_{1-6}$ alkylthio" and "$C_{1-6}$ alkylamino" are to be construed accordingly.

The expression "$C_{2-6}$ alkenyl" as used herein refers to straight-chained and branched alkenyl groups containing from 2 to 6 carbon atoms. Typical examples include vinyl, allyl, dimethylallyl and butenyl groups.

The expression "$C_{2-6}$ alkynyl" as used herein refers to straight-chained and branched alkynyl groups containing from 2 to 6 carbon atoms. Typical examples include ethynyl and propargyl groups.

Typical $C_{3-7}$ cycloalkyl groups include cyclopropyl, cyclobutyl, cyclopentyl and cyclohexyl.

Typical aryl groups include phenyl and naphthyl.

The expression "aryl($C_{1-6}$)alkyl" as used herein includes benzyl, phenylethyl, phenylpropyl and naphthylmethyl.

Suitable heterocycloalkyl groups include azetidinyl, pyrrolidinyl, piperidinyl, piperazinyl and morpholinyl groups.

Suitable heteroaryl groups include pyridinyl, quinolinyl, isoquinolinyl, pyridazinyl, pyrimidinyl, pyrazinyl, pyranyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyrimidinylmethyl, pyrazinylmethyl, quinolinylmethyl and isoquinolinylmethyl.

The term "halogen" as used herein includes fluorine, chlorine, bromine and iodine, especially fluorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

In particular, where M represents the residue of a pyrrolidine ring, and the substituent R is attached to the 2-position thereof, then the absolute stereochemical configuration of the carbon atom at the point of attachment of the moiety R is preferably as depicted in structure IA as follows:

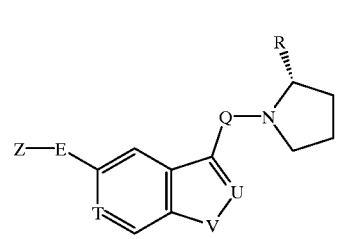
(IA)

wherein Z, E, Q, T, U, V and R are as defined above.

Moreover, where M represents the residue of a pyrrolidine ring, and the substituent R is attached to the 3-position thereof, then the absolute stereochemical configuration of the carbon atom at the point of attachment of the moiety R is preferably as depicted in structure IB as follows:

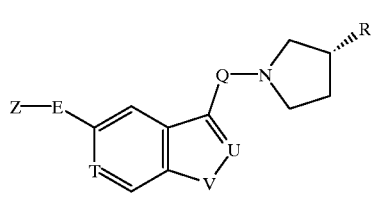
(IB)

wherein Z, E, Q, T, U, V and R are as defined above.

The optionally substituted five-membered heteroaromatic ring Z in formula I is suitably a 1,3-oxazole, 1,3-thiazole, imidazole, 1,2,4-oxadiazole, 1,3 4-oxadiazole, 1,2,4-thiadiazole, 1,3,4-thiadiazole, 1,2,3-triazole, 1,2,4-triazole or tetrazole ring. Preferably, the ring is a 1,3-oxazole, 1,3-thiazole, imidazole, 1,2,4-oxadiazole, 1,2,4-thiadiazole or 1,2,4-triazole ring, in particular an imidazol-1-yl, 1,2,4-triazol-1-yl or 1,2,4-triazol-4-yl moiety, and especially 1,2,4-triazol-1-yl or 1,2,4-triazol-4-yl.

Suitably, the five-membered heteroaromatic ring Z is unsubstituted. Examples of optional substituents which may typically be attached to the moiety Z includes methyl, ethyl, benzyl and amino.

Where E, Q and W, which may be the same or different, represent straight or branched alkylene chains, these may be, for example, methylene, ethylene, 1-methylethylene, propylene, 2-methylpropylene or butylene. In addition, Q may be substituted in any position by a hydroxy group giving rise, for example, to a hydroxymethyl-methylene, 2-hydroxypropylene or 2-hydroxymethyl-propylene linkage. Moreover, E and W may each independently represent a chemical bond. Where E represents a che(mical bond, the moiety Z is attached directly to the central fused bicyclic heteroaromatic ring system containing the variables T, U and V. Similarly, where W represents a chemical bond, the substituent R¹ is attached directly to the azetidine, pyrrolidine or piperidine ring of which M is the residue.

Suitably, E represents a chemical bond or a methylene linkage.

Suitably, Q represents an ethylene or propylene linkage.

Suitably, W represents a chemical bond or a methylene linkage.

The compound of formula I in accordance with the present invention is suitably an indole, benzofuran or benzthiophene derivative of formula IC, an indazole derivative of formula ID, or a pyrrolo[2,3-c]pyridine derivative of formula IE:

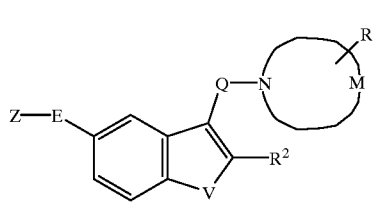
(IC)

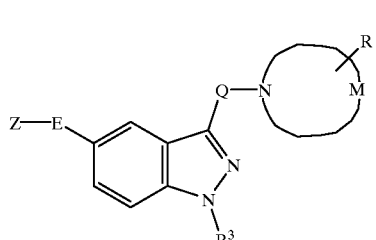
(ID)

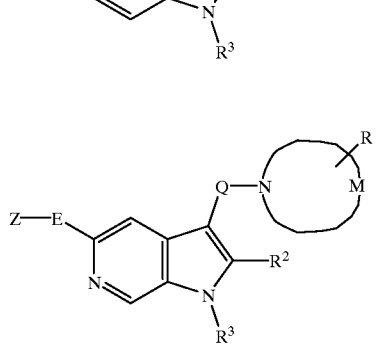
(IE)

wherein Z, E, Q, V, M, R, R² and R³ are as defined above.

Preferably, the compounds according to the invention are indole or pyrrolo[2,3-c]pyridine derivatives of formula IF:

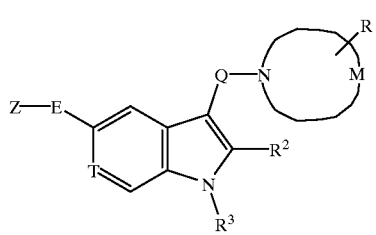
(IF)

wherein Z, E, Q, T, M, R, R² and R³ are as defined above, in particular wherein R² and R³ are both hydrogen.

Suitably, R² and R³ independently represent hydrogen or methyl, especially hydrogen.

Particular values of R⁴ include hydrogen, fluoro, chloro, cyano, nitro, trifluoromethyl, methyl, hydroxy, methoxy, acetyl, amino, methylamino, dimethylamino, acetylamino, methylsulphonylamino or methylaminosulphonylmethyl, especially hydrogen or fluoro.

Suitably, R⁵ represents hydrogen or methyl.

A particular sub-class of compounds according to the invention is represented by the compounds of formula IIA, and salts and prodrugs thereof:

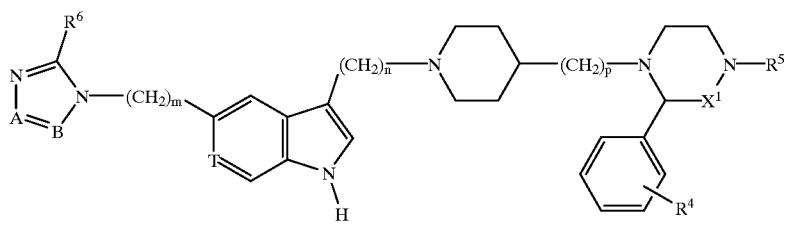

(IIA)

wherein
m is zero, 1, 2 or 3, preferably zero or 1;
n is 2, 3 or 4, preferably 2 or 3;
p is zero or 1;
T represents nitrogen or CH;
A represents nitrogen or CH;
B represents nitrogen or C—$R^7$;
$R^6$ and $R^7$ independently represent hydrogen, $C_{1-6}$ alkyl, $C_{2-6}$ alkenyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, amino, $C_{1-6}$ alkylamino, di($C_{1-6}$)alkylamino, halogen, cyano or trifluoromethyl;
$X^1$ represents $CH_2$ or C=O; and
$R^4$ and $R^5$ are as defined with reference to formula I above.

In relation to formula IIA, the substituent $R^4$ is suitably hydrogen or fluoro.

In relation to formula IIA, the substituent $R^5$ is suitably hydrogen or methyl.

Particular values of $R^6$ and $R^7$ include hydrogen, methyl, ethyl, benzyl and amino, especially hydrogen.

Another sub-class of compounds according to the invention is represented by the compounds of formula IIB, and salts and prodrugs thereof:

1-[3-(5-(1,2,4-triazol-4-yl)-1H-indol-3-yl)propyl]-4-(benzimidazol-2-on-1-yl)piperidine;
1-[3-(5-(1,2,4-triazol-4-yl)-1H-indol-3-yl)propyl]-4-[6-(4-fluorophenyl)-4-methyl-3-oxopiperazin-1-yl]piperidine;
1-[3-(5-(1,2,4-triazol-4-yl)-1H-indol-3-yl)propyl]-4-[2-(4-fluorophenyl)-4-methylpiperazin-1-yl]piperidine;
1-[2-(5-(1,2,4-triazol-1-ylmethyl)-1H-indol-3-yl)ethyl]-3(R)-(3(R)-phenylmorpholin-4-ylmethyl)pyrrolidine;
and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically

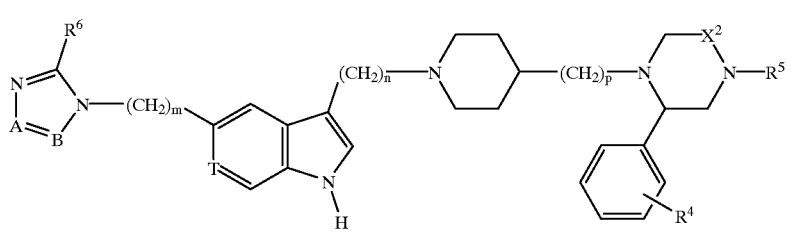

(IIB)

wherein
$X^2$ represents $CH_2$ or C=O;
m, n, p, T, A, B and $R^6$ are as defined with reference to formula IIA above; and
$R^4$ and $R^5$ are as defined with reference to formula I above.

In relation to formula IIB, the substituent $R^4$ is suitably hydrogen or fluoro.

In relation to formula IIB, the substituent $R^5$ is suitably hydrogen or methyl.

Specific compounds within the scope of the present invention include:
1-[3-(5-(1,2,4-triazol-4-yl)-1H-indol-3-yl)propyl]-4-(3-oxo-2-phenylpiperazin-1-yl)methylpiperidine;
1-[3-(5-(1,2,4-triazol-4-yl)-1H-indol-3-yl)propyl]-4-(4-methyl-2-phenylpiperazin-1-yl)piperidine;

acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former.

The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compounds may be administered or a regimen of 1 to 4 times per day.

The compounds according to the invention wherein T represents CH, U represents C—$R^2$ and V represents N—$R^3$, corresponding to the indole derivatives of formula IC as defined above wherein V represents N—$R^3$, may be prepared by a process which comprises reacting a compound of formula III:

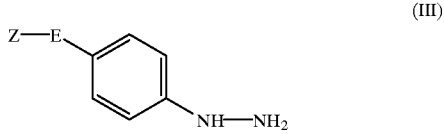

(III)

wherein Z and E are as defined above; with a compound of formula IV, or a carbonyl-protected form thereof:

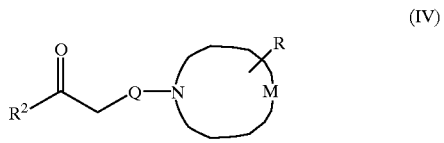

(IV)

wherein $R^2$, Q, M and R are as defined above; followed, where required, by N-alkylation by standard methods to introduce the moiety $R^3$.

The reaction between compounds III and IV, which is an example of the well-known Fischer indole synthesis, is suitably carried out by heating the reagents together under mildly acidic conditions, e.g. 4% sulphuric acid at reflux.

Suitable carbonyl-protected forms of the compounds of formula IV include the dimethyl acetal or ketal derivatives. Where the alkylene chain Q is substituted by a hydroxy group, this group may condense with the carbonyl moiety in compound IV whereby the carbonyl moiety is protected in the form of a cyclic hemiacetal.

The Fischer reaction between compounds III and IV may be carried out in a single step, or may proceed via an initial non-cyclising step at a lower temperature to give an intermediate of formula V:

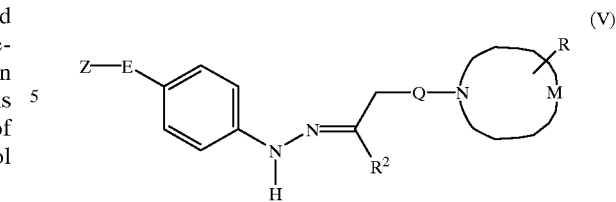

(V)

wherein Z, E, Q, $R^2$, M and R are as defined above; followed by cyclisation using a suitable reagent, e.g. a polyphosphate ester.

The intermediates of formula IV, or carbonyl-protected forms thereof, may be prepared by reacting a compound of formula VI, or a carbonyl-protected form thereof, with a compound of formula VII:

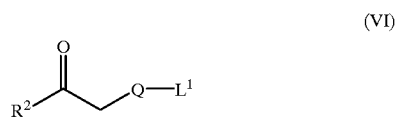

(VI)

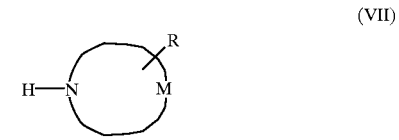

(VII)

wherein Q, $R^2$, M and R are as defined above, and $L_1$ represents a suitable leaving group.

The leaving group $L^1$ is suitably a halogen atom, e.g. chlorine or bromine.

Where $L^1$ represents a halogen atom, the reaction between compounds VI and VII is conveniently effected by stirring the reactants under basic conditions in a suitable solvent, for example sodium carbonate or potassium carbonate in 1,2-dimethoxyethane or N,N-dimethylformamide, or triethylamine in tetrahydrofuran or acetonitrile, optionally in the presence of sodium iodide.

In an alternative procedure, the compounds according to the invention may be prepared by a process which comprises reacting a compound of formula VII as defined above with a compound of formula VIII:

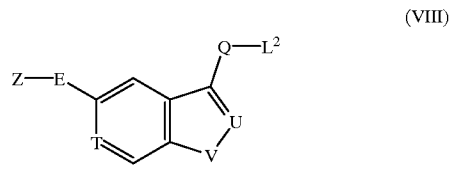

(VIII)

wherein Z, E, Q, T, U and V are as defined above, and $L^2$ represents a suitable leaving group.

The leaving group $L^2$ is suitably an alkylsulphonyloxy or arylsulphonyloxy group, e.g. methanesulphonyloxy (mesyloxy) or p-toluenesulphonyloxy (tosyloxy).

Where $L^2$ represents an alkylsulphonyloxy or arylsulphonyloxy group, the reaction between compounds VII and VIII is conveniently carried out in a suitable solvent such as isopropanol or 1,2-dimethoxy-ethane, typically in the presence of a base such as sodium carbonate or potassium carbonate, optionally in the presence of sodium iodide.

In one representative approach, the compounds of formula VIII wherein T and U both represent CH, V represents NH and $L^2$ represents a mesyloxy or tosyloxy group may be prepared by the sequence of steps illustrated in th(e following reaction scheme (cf. Larock and Yum, *J. Am. Chem. Soc.*, 1991, 113, 6689):

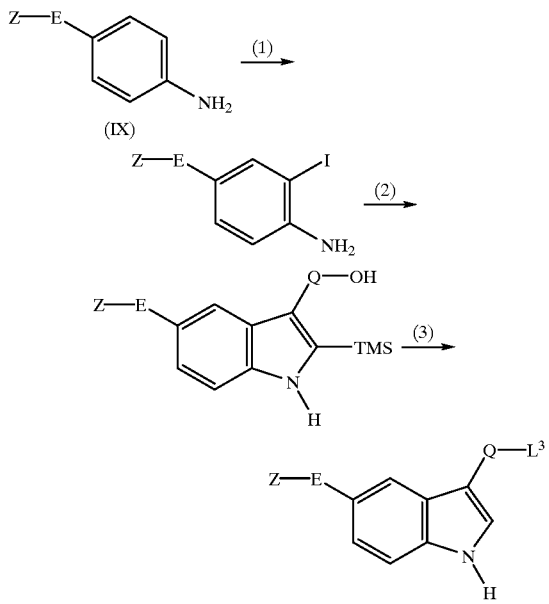

wherein Z, E and Q are as defined above, $L^3$ represents mesyloxy or tosyloxy, and TMS is an abbreviation for trimethylsilyl.

In Step 1 of the reaction scheme, the aniline derivative IX is treated with iodine monochloride, advantageously in methanol in the presence of a base such as calcium carbonate, in order to introduce an iodine atom ortho to the amine moiety. Step 2 involves a palladium-mediated coupling reaction with the protected acetylene derivative TMS—C≡—C—Q—OH, typically using palladium acetate and triphenylphosphine in the presence of lithium chloride and sodium carbonate, suitably in N,N-dimethylformamide at an elevated temperature. This is followed in Step 3 by removal of the TMS moiety, ideally in refluxing methanolic hydrochloric acid; followed in turn by mesylation or tosylation, suitably by using mesyl chloride or tosyl chloride respectively in pyridine.

In another representative approach, the compounds of formula VIII wherein T and U both represent CH, V represents NH, Q represents a propylene chair, and $L^2$ represents a mesyloxy or tosyloxy group may be prepared by reacting 3,4-dihydro-2H-pyran with a compound of formula III as defined above or a salt thereof, under a variant of the Fischer reaction conditions as described above for the reaction between compounds III and IV; followed by mesylation or tosylation of the 3-hydroxypropyl-indole derivative thereby obtained, typically by treatment with mesyl chloride or tosyl chloride under standard conditions.

The Fischer reaction with 3,4-dihydro-2H-pyran is suitably brought about by heating the hydrazine derivative III or an acid addition salt thereof, typically the hydrochloride salt, in an inert solvent such as dioxan, advantageously in the presence of a mineral acid such as hydrochloric acid or sulphuric acid, or a Lewis acid such as zinc chloride, at the reflux temperature of the solvent.

In a further procedure, the compounds according to the invention wherein T represents CH, U represents nitrogen and V represents N—$R^3$, corresponding to the indazole derivatives of formula ID as defined above, may be prepared by a process which comprises cyclising a compound of formula X:

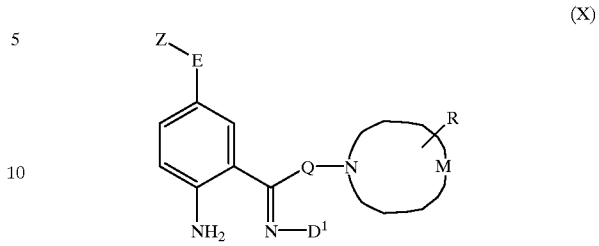

wherein Z, E, Q, M and R are as defined above, and $D^1$ represents a readily displaceable group; followed, where required, by N-alkylation by standard methods to introduce the moiety $R^3$.

The cyclisation of compound X is conveniently achieved in a suitable organic solvent at an elevated temperature, for example in a mixture of m-xylene and 2,6-lutidine at a temperature in the region of 140° C.

The readily displaceable group $D^1$ in the compounds of formula X suitably represents a $C_{1-4}$ alkanoyloxy group, preferably acetoxy. Where $D^1$ represents acetoxy, the desired compound of formula X may be conveniently prepared by treating a carbonyl compound of formula XI:

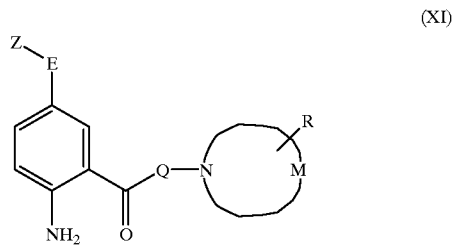

wherein Z, E, Q, M and R are as defined above; or a protected derivative thereof, preferably the N-formyl protected derivative; with hydroxylamine hydrochloride, advantageously in pyridine at the reflux temperature of the solvent; followed by acetylation with acetic anhydride, advantageously in the presence of a catalytic quantity of 4-dimethylaminopyridine, in dichloromethane at room temperature.

The N-formyl protected derivatives of the intermediates of formula XI may conveniently be prepared by ozonolysis of the corresponding indole derivative of formula XII:

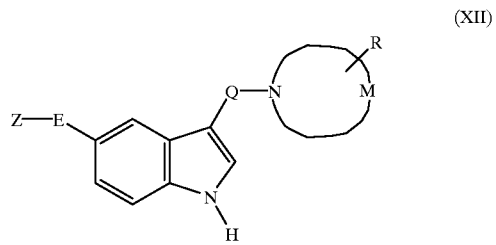

wherein Z, E, Q, M and R are as defined above; followed by a reductive work-up, advantageously using dimethylsulphide.

The indole derivatives of formula XII may be prepared by methods analogous to those described in the accompanying Examples, or by procedures well known from the art.

In a still further procedure, the compounds according to the invention wherein T represents CH, U represents C—R² and V represents oxygen or sulphur, corresponding to the benzofuran or benzthiophene derivatives of formula IC wherein V is oxygen or sulphur respectively, may be prepared by a process which comprises cyclising a compound of formula XIII:

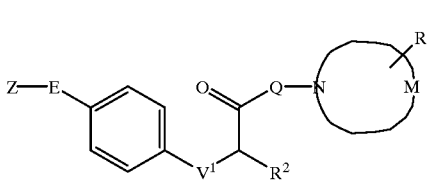

(XIII)

wherein Z, E, Q, R², M and R are as defined above, and V¹ represents oxygen or sulphur.

The cyclisation of compound XIII is conveniently effected by using polyphosphoric acid or a polyphosphate ester, advantageously at an elevated temperature.

The compounds of formula XIII may be prepared by reacting a compound of formula XIV with a compound of formula XV:

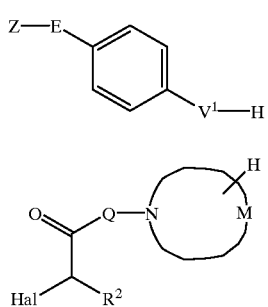

(XIV)

(XV)

wherein Z, E, Q, R², V¹, M and R are as defined above, and Hal represents a halogen atom.

The reaction is conveniently effected in the presence of a base such as sodium hydroxide.

The hydroxy and mercapto derivatives of formula XIV may be prepared by a variety of methods which will be readily apparent to those skilled in the art. One such method is described in EP-A-0497512.

In a yet further procedure, the compounds according to the invention may be prepared by, a process which comprises reducing a compound of formula XVI:

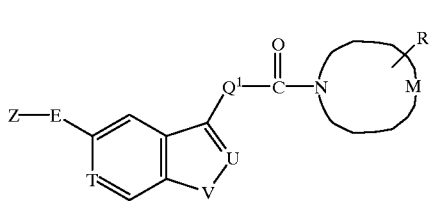

(XVI)

wherein Z, E, T, U, V, M and R are as defined above, and —Q¹—CH₂ corresponds to the moiety Q as defined above.

The reaction is suitably carried out by treating the compound of formula XVI with a reducing agent such as lithium aluminium hydride in an appropriate solvent, e.g. diethyl ether, tetrahydrofuran or mixtures thereof.

The compounds of formula XVI above may suitably be prepared by reacting a compound of formula VII as defined above with the appropriate compound of formula XVII:

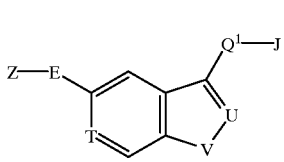

(XVII)

wherein Z, E, T, U, V and Q¹ are as defined above, and J represents a reactive carboxylate moiety.

Suitable values for the reactive carboxylate moiety J include esters, for example $C_{1-4}$ alkyl esters; acid anhydrides, for example mixed anhydrides with $C_{1-4}$ alkanoic acids; acid halides, for example acid chlorides; and acylimidazoles.

By way of example, the intermediates of formula XVII above wherein J is an acid chloride moiety may be prepared by treating the corresponding carboxylic acid derivative with thionyl chloride in toluene. Similarly, the intermediates of formula XVII wherein J is an acylimidazole moiety may be prepared by treating the corresponding carboxylic acid derivative with 1,1'-carbonyldiimidazole. Alternatively, the reactive carboxylate moiety J may be obtained by treating the corresponding compound wherein J is carboxy with 1-(3-dimethylaminopropyl)-3-ethylcarbodiimide hydrochloride and 1-hydroxybenzotriazole hydrate, optionally in the presence of triethylamine; the resulting activated carboxylate intermediate may then suitably be reacted in situ with the required compound of formula VII.

In an additional procedure, the compounds according to the invention may be prepared by a process which comprises reacting a compound of formula H—R¹ with a compound of formula XVIII:

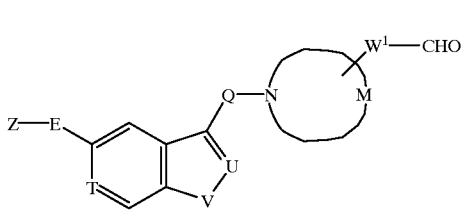

(XVIII)

wherein Z, E, T, U, V, Q, M and R¹ are as defined above, and —W¹—CH₂ corresponds to the moiety W as defined above; in the presence of a reducing agent.

A suitable reducing agent for effecting this transformation is sodium cyanoborohydride, in which case the reaction is conveniently carried out in methanol/acetic acid.

The hydrazine derivatives of formula III above may be prepared by methods analogous to those described in WO-A-94/02477. EP-A-0438230 and EP-A-0497512, as also may the aniline derivatives of formula IX.

Where they are not commercially available, the starting materials of formula VI, VII, XV, XVII, XVIII and H—R¹ may be prepared by the methods described in the accompanying Examples, or by analogous procedures which will be apparent to those skilled in the art.

It will be understood that any compound of formula I initially obtained from any of the above processes may, where appropriate, subsequently be elaborated into a further compound of formula I by techniques known from the art. For example, a compound of formula I wherein R³ is hydrogen initially obtained may be converted into a compound of formula I wherein $R^3$ represents $C_{1-6}$ alkyl by standard alkylation techniques, for example by treatment with an alkyl iodide, e.g. methyl iodide, typically under basic conditions, e.g. sodium hydride in dimethylformamide, or triethylamine in acetonitrile.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973: and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with the present invention potently and selectively bind to the $5\text{-HT}_{1D_\alpha}$ receptor subtype, inhibit forskolin-stimulated adenylyl cyclase activity, and stimulate [$^{35}$S]-GTPγS binding to membranes from clonal cell lines expressing human cloned receptors.

$5\text{-HT}_{1D_\alpha}/5\text{-HT}_{1D_\beta}$ Radioligand Binding

Chinese hamster ovary (CHO) clonal cell lines expressing the human $5\text{-HT}_{1D_\alpha}$ and $5\text{-HT}_{1D_\beta}$ receptors were harvested in PBS and homogenised in ice cold 50 mM Tris-HCl (pH 7.7 at room temperature) with a Kinematica polytron and centrifuged at 48,000 g at 4° C. for 11 min. The pellet was then resuspended in 50 mM Tris-HCl followed by a 10 min incubation at 37° C. Finally the tissue was recentrifuged at 48,000 g, 4° C. for 11 min and tile pellet resuspended, in assay buffer (composition in mM: Tris-HCl 50, pargyline 0.01, CaCl$_2$ 4; ascorbate 0.1%; pH 7.7 at room temperature) to give the required volume immediately prior to use (0.2 mg protein/ml). Incubations were carried out for 30 min at 37° C. in the presence of 0.02–150 nM [$^3$H]-5-HT for saturation studies or 2–5 nM [$^3$H]-5-HT for displacement studies. The final assay volume was 1 ml. 5-HT (10 μM) was used to define non-specific binding. The reaction was initiated by the addition of membrane and was terminated by rapid filtration through Whatman GF/B filters (presoaked in 0.3% PEI/0.5% Triton X) followed by 2×4 ml washings with 50 mM Tris-HCl. The radioactive filters were then counted on a LKB beta or a Wallac beta plate counter. Binding parameters were determined by non-linear, least squares regression analysis using an iterative curve fitting routine, from which IC$_{50}$ (the molar concentration of compound necessary to inhibit binding by 50%) values could be calculated for each test compound. The IC$_{50}$ values for binding to the $5\text{-HT}_{1D_\alpha}$ receptor subtype obtained for the compounds of the accompanying Examples were below 100 nM in each case. Furthermore, the compounds of the accompanying Examples were all found to possess a selective affinity for the $5\text{-HT}_{1D_\alpha}$ receptor subtype of at least 10-fold relative to the $5\text{-HT}_{1D_\beta}$ subtype.

$5\text{-HT}_{1D_\alpha}/5\text{-HT}_{1D_\beta}$ Adenylyl Cyclase Assay

Studies were performed essentially as described in *J. Pharmacol. Exp. Ther.*, 1986, 238, 248. CHO clonal cell lines expressing the human cloned $5\text{-HT}_{1D_\alpha}$ and $5\text{-HT}_{1D_\beta}$ receptors were harvested in PBS and homogenised, using a motor driven teflon/glass homogeniser, in ice cold Tris HCl-EGTA buffer (composition in mM: Tris HCl 10, EGTA 1, pH 8.0 at room temperature) and incubated on ice for 30–60 min. The tissue was then centrifuged at 20,000 g for 20 min at 4° C., the supernatant discarded and the pellet resuspended in Tris HCl-EDTA buffer (composition in mM: Tris HCl 50, EDTA 5, pH 7.6 at room temperature) just prior to assay. The adenylyl cyclase activity was determined by measuring the conversion of α-[$^{33}$P]-ATP to [$^{33}$P]-cyclic AMP. A 10 μl aliquot of the membrane suspension was, incubated, for 10–15 min, in a final volume of 50 μl, at 30° C., with or without forskolin (10 μM), in the presence or absence of test compound. The incubation buffer consisted of 50 mM Tris HCl (pH 7.6 at room temperature), 100 mM NaCl, 30 μM GTP, 50 μM cyclic AMP, 1 mM dithiothreitol, 1 mM ATP, 5 mM MgCl$_2$, 1 mM EGTA, 1 mM 3-isobutyl-1-methylxanthine, 3.5 mM creatinine phosphate, 0.2 mg/ml creatine phosphokinase, 0.5–1 μCi α-[$^{33}$P]-ATP and 1 nCi [$^3$H]-cyclic AMP. The incubation was initiated by the addition of membrane, following a 5 min preincubation at 30° C., and was terminated by the addition of 100 μl SDS (composition in mM: sodium lauryl sulphate 2%, ATP 45, cyclic AMP 1.3, pH 7.5 at room temperature). The ATP and cyclic AMP were separated on a double column chromatography system (*Anal. Biochem.*, 1974, 58, 541). Functional parameters were determined using a least squares curve fitting programme ALLFIT (*Am. J. Physiol.*, 1978, 235, E97) from which E$_{max}$ (maximal effect) and EC$_{50}$ (the molar concentration of compound necessary to inhibit the maximal effect by 50%) values were obtained for each test compound. Of those compounds which were tested in this assay, the EC$_{50}$ values for the $5\text{-HT}_{1D_\alpha}$ receptor obtained for the compounds of the accompanying Examples were below 500 nM in each case. Moreover, the compounds of the accompanying Examples which were tested were all found to possess at least a 10-fold selectivity for the $5\text{-HT}_{1D_\alpha}$ receptor subtype relative to the $5\text{-HT}_{1D_\beta}$ subtype.

$5\text{-HT}_{1D_\alpha}/5\text{-HT}_{1D_\beta}$ GTPγS Binding

Studies were performed essentially as described in *Br. J. Pharmacol.*, 1993, 109, 1120. CHO clonal cell lines expressing the human cloned $5\text{-HT}_{1D_\alpha}$ and $5\text{-HT}_{1D_\beta}$ receptors were harvested in PBS and homogenised using a Kinematica polytron in ice cold 20 mM HEPES containing 10 mM EDTA, pH 7.4 at room temperature. The membranes were then centrifuged at 40,000 g, 4° C. for 15 min. The pellet was then resuspended in ice cold 20 mM HEPES containing 0.1 mM EDTA, pH 7.4 at room temperature and recentrifuged at 40,000 g, 4° C. for 15–25 minutes. The membranes were then resuspended in assay buffer (composition in mM: HEPES 20, NaCl 100, MgCl$_2$ 10, pargyline 0.01; ascorbate 0.1%; pH 7.4 at room temperature) at a concentration of 40 μg protein/ml for the $5\text{-HT}_{1D_\alpha}$ receptor transfected cells and 40–50 μg protein/ml for the $5\text{-HT}_{1D_\beta}$ receptor transfected cells. The membrane suspension was then incubated, in a volume of 1 ml, with GDP (100 μM for $5\text{-HT}_{1D_\alpha}$ receptor transfected cells, 30 μM for the $5\text{-HT}_{1D_\beta}$ receptor transfected cells) and test compound at 30° C. for 20 min and then transferred to ice for a further 15 min. [$^{35}$S]-GTPγS was then added at a final concentration of 100 pM and the samples incubated for 30 min at 30° C. The reaction was initiated by the addition of membrane and was terminated by rapid filtration through Whatman GF/B filters and washed with 5 ml water. The radioactive filters were then counted on a LKB beta counter. Functional parameters were determined by a non-linear, least squares regression analysis using an iterative curve fitting routine, from which $E_{max}$ (maximal effect) and $EC_{50}$ (the molar concentration of compound necessary to inhibit the maximal effect by 50%) values were obtained for each test compound. Of those compounds which were tested in this assay, the $EC_{50}$ values for the 5-$HT_{1D_\alpha}$ receptor obtained for the compounds of the accompanying Examples were below 500 nM in each case. Moreover, the compounds of the accompanying Examples which were tested were all found to possess at least a 10-fold selectivity for the 5-$HT_{1D_\alpha}$ receptor subtype relative to the 5-$HT_{1D_\beta}$ subtype.

INTERMEDIATE 1
1-{3-[5-(1,2,4-Triazol-4-yl)-1H-indol-3-yl]propyl}-4-(hydroxymethyl)piperidine 1. 4-(1,2,4-Triazol-4-yl)phenylhydrazine
   Prepared as described in WO 94/03446, Example 1.
2. 5-[4-(Hydroxymethyl)piperidin-1-yl]pentanal dimethyl acetal To a cooled (0° C.) and stirred suspension of isonipecotic acid (25.83 g, 200 mmol), in anhydrous THF (100 ml) was added lithium aluminium hydride (1M in THF; 200 ml), under a nitrogen atmosphere. The reaction was allowed to attain room temperature and it was stirred for 18 h, then refluxed for a further 4 h. The reaction was quenched by sequential addition of water (7.5 ml), 15% sodium hydroxide solution (7.5 ml) and water (15 ml). The reaction was filtered to remove a granular precipitate and the filtrate was concentrated under vacuum to give 11.24 g of 4-(hydroxymethyl)piperidine as a colourless oil.

A mixture of 5-chloropentanal dimethyl acetal (20.4 g, 122.4 mmol), anhydrous potassium carbonate (16.9 g, 122.4 mmol) and 4-(hydroxymethyl)piperidine (15.7 g, 136.0 mmol) in anhydrous dimethylformamide (150 ml) was stirred at 80° C. for 20 h, under nitrogen. After cooling, water (100 ml) was added and the mixture extracted with ethyl acetate (4×100 ml). The combined extracts were washed with brine (2×100 ml), dried ($Na_2SO_4$) and concentrated. Flash chromatography of the residue (silica gel, dichloromethane-methanol-ammonia, 90:10:1) afforded the title compound (18.7 g, 56%) as a pale yellow oil; $\delta_H$ (360 MHz, DMSO-$d_6$) 1.10 (2H, m), 1.28 (2H, m), 1.39 (2H, m), 1.48 (2H, m), 1.60 (2H, br d), 1.77 (2H, t), 2.20 (2H, t), 2.80 (2H, br d), 3.21 (8H, m), 4.31 (1H, t), 4.37 (1H, t).

3. 1-{3-[5-(1,2,4-Triazol-4-yl)-1H-indol-3-yl]propyl}-4-(hydroxymethyl) piperidine A solution of the preceding acetal (18.6 g, 75.9 mmol) and 4-(1,2,4-triazol-4-yl)phenylhydrazine (15.98 g, 91.2 mmol) in 4% aqueous sulphuric acid (1 l) was refluxed for 18 h. After cooling to room temperature, the solution was basified with 4N sodium hydroxide (ca 300 ml) and the mixture was extracted with n-butanol (3×300 ml). The combined organic extracts were concentrated and the resulting residue was purified by flash chromatography, (silica gel, dichloromethane-methanol-ammonia, 90:10:1) to give 9.8 g (38%) of the title compound as a yellow foam; $\delta_H$ (250 MHz, DMSO-$d_6$) 1.11 (2H, m), 1.30 (1H, m), 1.60 (2H, d), 1.80 (4H, m), 2.29 (2H, t), 2.70 (2H, t), 2.84 (2H, d), 3.22 (2H, t), 4.40 (1H, t), 7.26–7.31 (2H, m), 7.46 (1H, d), 7.78 (1H, d), 9.02 (2H, s), 11.08 (1H, s).

INTERMEDIATE 2
3-[5-(1,2,4-Triazol-4-yl)-1H-indol-3-yl]propan-1-ol

A solution of 4-(1,2,4-triazol-4-yl)phenylhydrazine (25 g, 143 mmol) in dioxan (250 ml) was treated with dihydropyran (24 g, 286 mmol) followed by 1M hydrochloric acid (150 ml) and heated at reflux for 18 h. The reaction mixture was evaporated, treated with toluene then re-evaporated. Inorganic solids were removed by treating the residue with a mixture of methanol and acetonitrile. The mother liquors were purified by column chromatography on silica using dichloromethane/methanol (9:1→4:1) as the eluant. The compound was recrystallised from acetonitrile to afford the title compound as a colourless solid (10.24 g, 30%); mp 205–207° C. (Found: C, 64.37; H, 5.76; N, 22.83. $C_{13}H_{14}N_4O$ requires: C, 64.45; H, 5.82; N, 23.13%). $\delta_H$ (360 MHz, DMSO-$d_6$) 1.81 (2H, q, J=7 Hz, $CH_2$), 2.75 (2H, t, J=8 Hz, $CH_2$), 3.46 (2H, dt, $J_1$=6, $J_2$=5 Hz, $CH_2$), 4.43 (1H, t, J=5 Hz, OH), 7.26 (1H, d, J=2 Hz, Ar—H), 7.29 (1H, dd, $J_1$=9, $J_2$=2 Hz, Ar—H), 7.47 (1H, d, J=9 Hz, Ar—H), 7.77 (1H, d, J=2 Hz, Ar—H), 9.01 (2H, s, triazole-H), 11.05 (1H, br s, indole NH); m/z (CI) 243 ($M^+$+1).

EXAMPLE 1
(±)-1-{3-[5-(1,2,4-Triazol-4-yl)-1H-indol-3-yl]propyl}-4-[(3-oxo-2-phenylpiperazin-1-yl)methyl]piperidine. 1.8 Hydrogen Oxalate To a solution of Intermediate 1 (2.0 g, 5.89 mmol) in a mixture of anhydrous dimethyl sulphoxide (50 ml) and anhydrous triethylamine (5.7 ml, 41.2 mmol) was added portionwise, under nitrogen, solid sulphur trioxide pyridine complex (3.37 g, 21.2 mmol) over 30 minutes. After 2 h of stirring, the mixture was cooled to 0° C. and quenched with saturated aqueous potassium carbonate (10 ml). The mixture was partitioned between water (60 ml) and n-butanol (150 ml), and the organic layer was concentrated to a third of its original volume before being diluted with methanol (40 ml). Acetic acid (2 ml, 35.3 mmol) and (±)-3-oxo-2-phenylpiperazine (J. Med. Chem., 1966, 181) (1.14 g, 6.48 mmol) were added followed, after 15 minutes, by sodium cyanoborohydride (407 mg, 6.48 mmol). After 18 h of stirring at room temperature, aqueous potassium carbonate was added and volatiles were removed under vacuum. The residue was partitioned between water and n-butanol and the organic phase was concentrated under vacuum. Flash chromatography of the residue (silica gel, dichloromethane-methanol-ammonia, 95:5:1) gave the title compound free base (737 mg, 25%) as a pale yellow solid. The oxalate salt was prepared from methanol-diethyl ether, mp 125–127° C. (Found: C, 59.30; H, 5.91; N, 14.74. $C_{29}H_{35}N_7O$×1.8 $C_2H_2O_4$ requires: C, 59.35; H, 5.90; N, 14.86%). m/z (ES) 498 ($M^+$+1).

EXAMPLE 2
(±)-1-{3-[5-(1,2,4-Triazol-4-yl)-1H-indol-3-yl]propyl}-4-(4-methyl-2-phenylpiperazin-1-yl)piperidine. Oxalate salt
1. (±)-1-tert-Butyloxycarbonyl-4-(3-oxo-2-phenylpiperazin-1-yl)piperidine A mixture of (±)-3-oxo-2-phenylpiperazine (J. Med. Chem. 1966, 181) (3.0 g, 17 mmol). N-tert-butyloxycarbonyl-4-piperidone (3.39 g, 17 mmol) and titanium isopropoxide (6 ml, 20.4 mmol) was stirred at room temperature, under nitrogen for 20 minutes. The viscous mixture was diluted with tetrahydrofuran (20 ml) and stirred for a further 2 h. Anhydrous methanol (10 ml) was added followed by sodium cyanoborohydride (1.07 g, 17 mmol) and the mixture was stirred for 18 h before solvents were removed under vacuum. The residue was partitioned between 15% aqueous sodium hydroxide and ethyl acetate, filtered through celite and the organic phase was separated washed with brine (2×), dried (MgSO$_4$) and concentrated. Flash chromatography (silica gel, dichloromethane-methanol-ammonia, 98:2:0.2) yielded a mixture of the required product and N-tert-butyloxycarbonyl- 4-piperidinol (1.5 g). This mixture was dissolved in dichloromethane (20 ml) and trifluoroacetic acid (5 ml) and was allowed to stand at room temperature for 18 h. The solvents were removed under vacuum and the residue purified by flash chromatography (silica gel, dichloromethane-methanol-ammonia, 85:15:1.5) to give (±)-4-(3-oxo-2-phenylpiperazin-1-yl) piperidine (185 mg) as a viscous oil. A solution of this amine (179 mg, 0.69 mmol) and di-tert-butyldicarbonate (158 mg, 0.72 mmol) in dichloromethane (10 ml) was stirred at room temperature for 18 h. The solvent was removed under vacuum and the residue purified by flash chromatography (silica gel, dichloromethane-methanol-ammonia, 96:3.6:0.4) to give the title compound (205 mg) as a viscous yellow oil; $\delta_H$(360 MHz, CDCl$_3$) 1.44 (9H, s), 1.47–1.57 (3H, m), 1.79 (1H, m), 2.48 (3H, m), 2.75 (1H, br t), 3.05 (1H, m), 3.34 (1H, m), 3.56 (1H, m), 4.13 (2H, m), 4.39 (1H, br s), 6.09 (1H, br s), 7.29–7.37 (3H, m), 7.46–7.48 (2H, m).

2. (±)-1-tert-Butyloxycarbonyl-4-(4-methyl-3-oxo-2-phenylpiperazin-1-yl)piperidine The compound from the previous step (200 mg, 0.56 mmol) was stirred at 0° C. in anhydrous dimethylformamide (5 ml) for 15 minutes with sodium hydride (27 mg, 0.67 mm). The mixture was allowed to attain room temperature and stirred for an additional 30 minutes. It was recooled (0° C.) and methyl iodide (83 mg, 0.58 mmol) was added. The mixture was allowed to warm to room temperature and stirred for a further 1 hour. A further aliquot, of methyl iodide (0.28 mmol) was added and the mixture stirred for 1.5 hours. The solvent was reduced by half the volume under vacuum and the mixture was partitioned between water and ethyl acetate. The aqueous layer was extracted thoroughly, and the combined extracts were dried (Na$_2$SO$_4$) and concentrated under vacuum to yield a yellow oil. Flash chromatography (silica gel. dichloromethane-methanol-ammonia. 96:4:0.4) gave the title product as a colourless foam (197 mg, 95%): $\delta_H$ (360 MHz, (CDCl$_3$) 1.45 (9H, s), 1.52 (3H, br m), 1.78–1.81 (1H. m), 2.49– 2.60 (3H, m), 2.72–2.80 (1H, m), 2.95 (3H, s), 3.02–3.07 (1H, m), 3.19–3.24 (1H, m), 3.56–3.61 (1H, m), 4.11 (2H, br m), 4.37 (1H, s), 7.25–7.34 (3H, m), 7.42–7.45 (2H, m).

3. (±)-1-tert-Butyloxycarbonyl-4-(4-methyl-2-phenylpiperazin-1-yl)piperidine

The compound from the previous step (195 mg, 0.52 mmol) was stirred at 0° C. in anhydrous tetrahydrofuran (6 ml). Lithium aluminium hydride (1M in THF; 2.1 ml, 2.1 mmol) was added dropwise via syringe. The mixture was stirred for 1 hour before water (80 µl), 15% sodium hydroxide (aq) (80 µl) and water (80 µl) were added successively, with stirring. The resulting precipitate was filtered and washed with tetrahydrofuran (20 ml). The combined filtrate and washings were reduced under vacuum to give the crude title product as a colourless oil (140 mg, 75%);$\delta_H$(250 MHz, CDCl$_3$) 1.44 (9H, s), 1.57–1.71 (3H, m), 1.83–1.88 (1H, m), 2.11–2.91 (12H, m), 3.68–3.77 (21H, m), 3.87 (2H, m), 7.29–7.32 (5H, m).

4. (±)-4-(4-Methyl-2-phenylpiperazin-1-yl)piperidine

The crude product from the previous step (140 mg, 0.39 mmol) was stirred in dichloromethane (10 ml) at room temperature, under nitrogen. Trifluoroacetic acid (2.5 ml) was added and the mixture was stirred for 1 hour. The solvents were removed under vacuum and the residue was partitioned between water and ethyl acetate. The water layer was extracted twice with ethyl acetate. The pH of the water layer was adjusted to pH10 with 4N sodium hydroxide and the basic aqueous solution was extracted with ethyl acetate (x3). The basic layer extracts were combined, dried (MgSO$_4$) and concentrated to yield the title product as a yellow oil (80 mg, 79%); $\delta_H$ (360 MHz, CDCl$_3$) 1.42–1.54 (2H, m), 1.68–1.74 (2H, m), 2.05 (1H, t), 2.15–2.26 (5H, m), 2.37–2.52 (2H, m), 2.61 (1H, dt), 2.87 (1H, dt), 2.87 (1H, m), 2.94 (1H, m), 3.04–3.07 (2H, m), 3.70 (1H, dd), 7.26–7.32 (5H, m).

5. (±)-1-{3-[5-1,2,4-Triazol-4-yl)-1H-indol-3-yl]propyl}-4-(4-methyl-2-phenylpiperazin-1-yl)piperidine. Oxalate salt A solution of Intermediate 2 (75 mg, 0.31 mmol) in anhydrous tetrahydrofuran (5 ml) was treated at 0° C. with anhydrous triethylamine (86 µl, 0.62 mmol) and methanesulphonyl chloride (48 µl, 0.62 mmol). The mixture was stirred at 0° C. for 1.5 hours before solids were filtered off and the solvent was removed under vacuum. The residue was partitioned between dichloromethane and water and the organic solution was dried (MgSO$_4$) and concentrated. The residue was dissolved in isopropanol (10 ml) and added to a suspension of the amine from step 4 (80 mg, 0.31 mmol), sodium iodide (462 mg, 3.1 mmol) and anhydrous potassium carbonate (42.5 mg, 0.31 mmol) in isopropanol (5 ml). The mixture was refluxed for 24 h and the solvent removed under vacuum. The residue was partitioned between aqueous potassium carbonate and ethyl acetate and the organic phase was washed with brine, dried (Na$_2$SO$_4$) and concentrated. Flash chromatography (silica gel, dichloromethane-methanol-ammonia, 95:5:0.5) of the residue, followed by preparative TLC purification (silica gel, dichloromethane-methanol-ammonia, 95:5:0.5) gave the title compound as a colourless thick oil (6 mg). The oxalate salt was prepared; mp 108–110° C. (methanol-diethyl ether); $\delta_H$ (500 MHz, DMSO-d$_6$) 1.58–1.69 (2H, m), 1.83–2.00 (4H, m), 2.59–2.80 (8H, m), 2.96–3.10 (6H, m), 3.34–3.55 (4H, m), 3.90 (1H, d), 7.32 (1H, s), 7.37–7.45 (6H, m), 7.54 (1H, d, J=8.0 Hz), 7.86 (1H, s), 9.52 (2H, s), 11.39 (1H, s); m/z (ES) 487 (M$^+$+1).

EXAMPLE 3

1-{3-[5-(1,2,4-Triazol-4-yl)-1H-indol-3-yl]propyl}-4-(2-keto-1-benzimidazolinyl)piperidine. 1.58 Hydrogen Oxalate To a stirred suspension of Intermediate 2 (300 mg, 1.24 mmol) in anhydrous tetrahydrofuran (50 ml) was added anhydrous triethylamine (0.35 ml, 2.48 mmol) followed by methanesulphonyl chloride (0.20 ml, 2.48 mmol). The mixture was stirred for 45 min under nitrogen before it was diluted with ethyl acetate (150 ml) and washed with brine (2×30 ml), then dried (MgSO$_4$) and concentrated. The remaining residue was dissolved in isopropanol (100 ml), and anhydrous potassium carbonate (206 mg, 1.49 mmol) and 4-(2-keto-1-benzimidazolinyl)piperidine (538 mg, 2.48 mmol) were added. The resulting mixture was refluxed under nitrogen for 62 hours, and the solvent was removed under vacuum. The remaining residue was partitioned between water (50 ml) and ethyl acetate (2×25 ml) and the combined organic phases were washed with brine (1×50 ml), dried (Na$_2$SO$_4$) and concentrated. Flash chromatography of the residue (silica gel, dichloromethane-methanol-ammonia, 90:10:1) afforded 290 mg (53%) of the title compound free base as a white foam. The oxalate salt was prepared; mp 140–147° C. (ethanol). (Found: C, 57.96; H, 5.34; N, 16.53. C$_{25}$H$_{27}$N$_7$O×1.58 C$_2$H$_2$O$_4$ requires: C, 57.94; H, 5.21; N, 16.80%). $\delta_H$ (360 MHz, DMSO-d$_6$) 1.88 (2H, br d), 2.04–2.16 (2H, m), 2.57–2.72 (2H, m), 2.82 (2H, t), 3.04–3.18 (4H, m), 3.60 (2H, br d), 4.44–4.56 (1H, m), 6.98–7.04 (4H, m), 7.26–7.40 (3H, m), 7.52 (1H, d, J=8.5

Hz), 7.85 (1H, d, J=2.0 Hz), 9.04 (2H, s), 10.92 (1H, s), 11.20 (1H, s); m/z (ES) 442 (M$^+$+1).

EXAMPLE 4

(±)-1-{3-[5-(1,2,4-Triazol-4-yl)-1H-indol-3-yl]propyl}-4-[6-(4-fluorophenyl)-4-methyl-3-oxopiperazin-1-yl]piperidine. Dihydrogen Oxalate 1.5 Hydrate 1. (±)-4-Fluorophenylglycine methyl ester. Hydrogen Chloride salt A stream of hydrogen chloride was passed through a suspension of (±)-4-fluorophenylglycine (20 g, 118 mmol) in anhydrous methanol (50 ml) using an ice bath to moderate an exotherm. Addition of hydrogen chloride was continued for 15 minutes after complete dissolution had occurred, and the reaction was then filtered and stored overnight. The resulting crystalline material was collected by filtration, washed with diethyl ether and dried over $P_2O_5$ to give the title compound as a colourless solid (19.4 g, 85%). $\delta_H$ (360 MHz, CDCl$_3$) 3.53 (3H, s), 3.79 (3H, s), 5.16 (1H, s), 7.09–7.16 (2H, m), 7.50–7.55 (2H, m).

2. (±)-1-tert-Butyloxycarbonyl-4-{[1-(4-fluorophenyl)-1-(methoxycarbonyl)methyl]amino}piperidine To a solution of the product from above (5 g, 23 mmol) in methanol (100 ml) was added sodium methoxide (1.24 g, 23 mmol). 1-tert-Butyloxycarbonyl-4-piperidone (4.53 g, 23 mmol) and acetic acid (4 ml, 69 mmol) were added to the solution of the amino acid free base, and the imine allowed to form for 10 minutes. Sodium cyanoborohydride (1.59 g, 15.3 mmol) was added in portions, and the reaction stirred overnight. The solvent was removed in vacuo, and the residue partitioned between 2N NaOH and ethyl acetate. The organic phase was separated, and the aqueous phase was reextracted with ethyl acetate (2×100 ml). The combined organic extracts were washed with brine, dried (MgSO$_4$), concentrated, and purified by chromatography on silica gel using 20% ethyl acetate—petroleum ether as eluant. The title compound was obtained as a viscous oil which crystallised slowly (5.76 g, 68%). $\delta_H$ (250 MHz, CDCl$_3$), 1.18–1.39 (2H, m), 1.43 (9H, s), 1.69–1.82 (2H, m), 2.48–2.60 (1H, m), 2.71–2.80 (2H, m), 3.78 (3H, s), 3.90–4.10 (2H, m), 4.50 (1H, s), 6.98–7.08 (2H, m), 7.26–7.39 (2H, m).

3. (±)-1-tert-Butyloxycarbonyl-4-{[1-(4-fluorophenyl)-1-(methylcarbamoyl)methyl]amino}piperidine A solution of the product from above (6 g, 16.4 mmol) in 2M methylamine-methanol (50 ml) was heated in a sealed glass tube at 90° C. for 18 hours. The solvent and volatiles were removed in vacuo to give the title compound as a colourless solid (6.15 g). $\delta_H$ (250 MHz, CDCl$_3$) 1.13–1.31 (2H, m), 1.33 (9H, s), 1.81–1.87 (2H, m), 2.52–2.60 (1H, m), 2.62–2.77 (2H, m), 2.80–2.84 (3H, d, J=5.0 Hz), 3.98–4.10 (2H, m), 4.29 (1H, s), 6.97–7.06 (2H, m), 7.13–7.17 (1H, m), 7.27–7.35 (2H, m).

4. (±)-1-tert-Butyloxycarbonyl-4-{[1-(4-fluorophenyl)-2-(methylamino)ethyl]amino}piperidine To a solution of the product from above (11.51 g, 31.5 mmol) in anhydrous tetrahydrofuran (200 ml) was added 1M borane-tetrahydrofuran complex (126 ml, 4 equivalents). The reaction was heated to reflux for 3 hours, concentrated in vacuo and treated cautiously with methanol until excess borane had been quenched. The reaction was reconcentrated, and then refluxed with 1:1 methanol-saturated aqueous potassium carbonate (200 ml). The reaction was concentrated to remove methanol, extracted with ethyl acetate, dried (MgSO$_4$), concentrated, and chromatographed using 3% methanol-dichloromethane and then methanol-dichloromethane-ammonia (10:89:1) as eluant. The title compound was obtained as a yellow oil (2.76 g, 25%) together with unreacted borane complex, which could be cleaved by heating to reflux in 4N NaOH-methanol (1:4, 150 ml) for 18 hours. Work up and purification as described above gave a further 5.5 g of product, $\delta_H$ (250 MHz, CDCl$_3$) 1.18–1.27 (2H, m), 1.43 (9H, s), 1.58–1.66 (1H, m), 1.87–1.92 (1H, m), 2.36–2.46 (4H, m), 2.58–2.72 (4H, m), 3.87–3.92 (3H, m), 6.99–7.66 (2H, m), 7.25–7.31 (2H, m).

5. (±)-1-tert-Butyloxycarbonyl-4-[6-(4-fluorophenyl)-4-methyl-3-oxo-piperazin-1-yl]piperidine A solution of the product from above (2.78 g, 7.9 mmol) in anhydrous tetrahydrofuran (300 ml) was cooled using an ice-sodium chloride bath. Hünig's base (3 ml) was added followed by dropwise addition of bromoacetyl bromide (0.758 ml). The reaction was allowed to attain room temperature, and stirred for 18 hours under a nitrogen atmosphere. The reaction was partially concentrated, washed with water, then brine, dried (MgSO$_4$), concentrated and chromatographed on silica gel using 5% methanol-diethyl ether. The title compound was isolated as a yellow oil (1.67 g, 54%). $\delta_H$ (250 MHz, CDCl$_3$) 1.32–1.67 (13H, m), 2.16–2.30 (1H, m), 2.46–2.52 (2H, in), 2.94 (3H, s), 3.16–3.23 (1H, m), 3.25–3.32 (1H, m), 3.37–3.55 (2H, m), 3 89–3.95 (1H, m), 3.95–4.14 (2H, m), 7.03–7.12 (2H, m), 7.28–7.36 (2H, m).

6. (±)-1-{3-[5-(1,2,4-Triazol-4-yl)-1H-indol-3-yl]-propyl}-4-[6-(4-fluorophenyl)-4-methyl-3-oxopiperazin-1-yl]piperidine. Dihydrogen Oxalate 1.5 Hydrate The product from above (400 mg, 1 mmol) was dissolved in dichloromethane (5 ml). Trifluoroacetic acid (5 ml) was added, and the reaction mixture allowed to stand at room temperature for 30 minutes. The reaction was concentrated and partitioned between ethyl acetate and 2N NaOH. The organic phase and extracts were dried (MgSO$_4$), and concentrated to give 4-[6-(4-fluorophenyl)-4-methyl-3-oxopiperazin-1-yl]piperidine. This was coupled to Intermediate 2 in a similar manner to that described in Example 3. Flash chromatography of the residue using dichloromethane-methanol-ammonia (94:5:1) as eluant gave the title compound as a beige foam (110 mg, 26%). The oxalate salt was prepared; m.p. 125° C. (softens) (ethanol-diethyl ether). (Found: C, 54.68: H, 5.88; N, 13.77. $C_{29}H_{34}FN_7O$. $2C_2H_2O_4$. 1.5H$_2$O requires: C, 54.84; H, 5.71; N, 13.56%), $\delta_H$ (360 MHz, DMSO-d$_6$+TFA) 1.6–2.08 (6H, m), 2.60–9.68 (1H, m), 2.70–2.78 (2H, m), 2.78–2.92 (5H, m), 2.92–3.04 (2H, m), 3.34–3.47 (2H, m), 3.48–3.70 (4H, m), 4.40–4.52(1H, m), 7.18–7.23 (2H, m), 7.30–7.32 (2H, m), 7.41–7.50 (3H m), 7.76–7.77 (1H, m), 8.99 (2H, s), 11.16 (1H, s); m/z (ES) 516 (M$^+$+1).

EXAMPLE 5

(±)-1-{3-[5-(1,2,4-Triazol-4-yl)-1H-indol-3-yl]propyl}-4-[2-(4-fluorophenyl)-4-methylpiperazin-1-yl]piperidine Dihydrogen Oxalate. 2.5 Hydrate 1. (±)-N-tert-Butyloxycarbonyl-4-[2-(4-fluorophenyl)-4-methylpiperazin-1-yl]piperidine A solution of the product from step 5, Example 4 (1.27 g, 3.24 mmol) was reacted in a similar manner to that described in step 4, Example 4. The title compound was obtained as a pale yellow oil (1.15 g, 94%). $\delta_H$ (250 MHz, CDCl$_3$) 1.25–1.53 (11H, m), 1.57–1.67 (2H, m), 1.96–2.05 (1H, m), 2.14–2.26 (4H, m), 2.40–2.50 (2H, m), 2.54–2.68 (1H, m), 2.73–2.88 (4H, m), 3.62–3.72 (1H, m), 3.98–4.14 (2H, m), 6.97–7.08 (2H, m), 7.26–7.33 (2H, m).

2. (±)-4-[2-(4-Fluorophenyl)-4-methylpiperazin-1-yl]piperidine

The product from above (1.15 g, 3 mmol) was deprotected in a similar manner to that described in step 4, Example 2 to give the title compound as a foam (804 mg, 95%). $\delta_H$ (250 MHz, DMSO-d$_6$) 1.10–1.22 (2H, m), 1.45–1.72 (2H, m), 1.76–1.88 (1H, m), 1.92–2.20 (5H, m), 2.22–2.40 (2H, m), 2.40–2.64 (2H, m), 2.66–2.86 (2H, m), 2.86–3.06 (2H, m), 3.64–3.69 (1H, m), 7.11–7.18 (2H, m), 7.34–7.40 (2H, m).

3. (±)-1-{3-[5-(1,2,4-Triazol-4-yl)-1H-indol-3-yl]propyl}-4-[2-(4-fluorophenyl)-4-methylpiperazin-1-yl]piperidine Dihydrogen Oxalate. 2.5 Hydrate The product from above (332 mg, 1.2 mmol) was reacted with Intermediate 2 in a similar manner to that described in Example 3; chromatography using dichloromethane-methanol-ammonia (89:10:1) as eluant gave the title compound as a clear foam (105 mg, 25%): $\delta_H$ (250 MHz, CDCl$_3$) 1.22–1.50 (1H, m), 1.52–1.64 (2H, m), 1.68–1.92 (5H, m), 1.94–2.04 (1H, m), 2.10–2.22 (1H, m), 2.25 (3H, s), 2.26–2.40 (3H, m), 2.59–2.68 (1H, m), 2.71–2.75 (3H, m), 2.83–2.86 (1H, m), 1.88–3.00 (3H, m), 3.66–3.68 (1H, m), 6.96–7.01 (2H, m), 7.11–7.14 (2H, m), 7.26–7.29 (2H, m), 7.44–7.46 (1H, m), 7.51–7.52 (1H, m), 8.44 (2H, s). The oxalate salt was prepared; m.p. 145° C. (softens) (ethanol-diethyl ether). (Found: C, 54.31; H, 6.29; N, 13.42. C$_{29}$H$_{36}$FN$_7$. 2C$_2$H$_2$O$_4$. 2.5H$_2$O requires: C, 54.54; H, 6.24; N, 13.49%).

I claim:

1. A compound of formula I, or a salt or prodrug thereof:

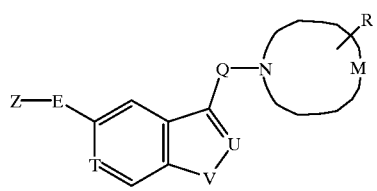

(I)

wherein

Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole;

E represents a chemical bond or a straight or branched alkylene chain containing from 1 to 4 carbon atoms;

Q represents a straight or branched alkylene chain containing from 1 to 4 carbon atoms, optionally substituted in any position by a hydroxy group;

T represents CH;

U represents C—R$^2$;

V represents N—R$^3$;

R$^2$ and R$^3$ independently represent hydrogen or C$_{1-6}$ alkyl;

M represents the, residue of an azetidine, pyrrolidine or piperidine ring;

R represents a group of formula —W—R$^1$;

W represents a chemical bond or a straight or branched alkylene chain containing from 1 to 4 carbon atoms; and R$^1$ represents a group of formula (a), (b), (c) or (d):

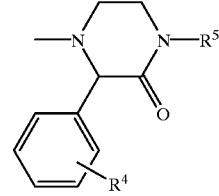

(a)

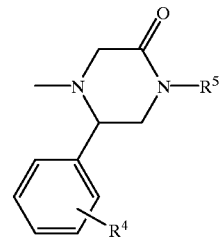

(b)

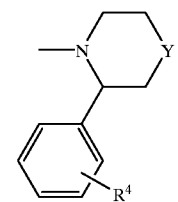

(c)

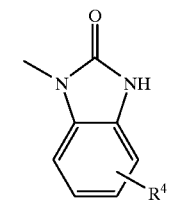

(d)

in which

Y represents oxygen or N—R$^5$;

R$^4$ represents hydrogen, halogen, cyano, nitro, trifluoromethyl, C$_{1-6}$ alkyl, hydroxy, C$_{1-6}$ alkoxy, C$_{2-6}$ alkylcarbonyl, amino, C$_{1-6}$ alkylamino, di(C$_{1-6}$) alkylamino, C$_{2-6}$ alkylcarbonylamino, C$_{1-6}$ alkylsulphonylamino or C$_{1-6}$ alkylaminosulphonylmethyl; and R$^5$ represents hydrogen or C$_{1-6}$ alkyl.

2. A compound as claimed in claim 1 represented by formula IIA, and salts and prodrugs thereof:

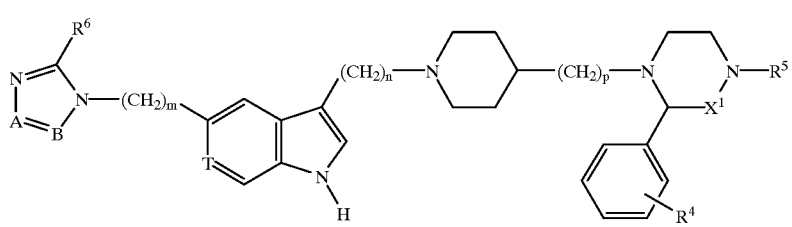

(IIA)

wherein m is zero, 1, 2 or 3;

n is 2, 3 or 4;

p is zero or 1;

T represents CH;

A represents nitrogen or CH;

B represents nitrogen or C—$R^7$;

$R^6$ and $R^7$ independently represent hydrogen, $C_{1-6}$ alkyl, $C_{2-6}$ alkenyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, amino, $C_{1-6}$ alkylamino, di($C_{1-6}$)alkylamino, halogen, cyano or trifluoromethyl;

$X^1$ represents $CH_2$ or C=O; and $R^4$ and $R^5$ are as defined in claim 1.

3. A compound as claimed in claim 1 represented by formula IIB, and salts and prodrugs thereof:

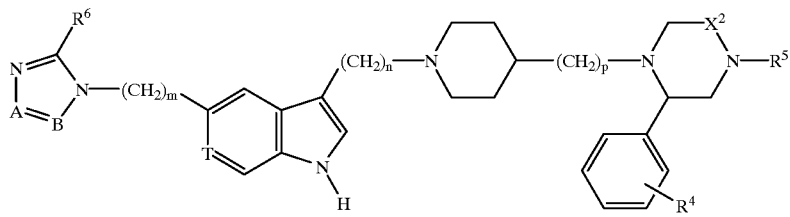

(IIB)

wherein $X^2$ represents $CH_2$ or C=O;

m, n, p, T, A, B and $R^6$ are as defined in claim 2; and $R^4$ and $R^5$ are as defined in claim 1.

4. A compound as claimed in claim 1 wherein $R^4$ represents hydrogen or fluoro.

5. A compound as claimed in claim 1 wherein $R^5$ represents hydrogen or methyl.

6. A compound selected from:
1-[3-(5-(1,2,4-triazol-4-yl)-1H-indol-3-yl)propyl]-4-(3-oxo-2-phenylpiperazin-1-yl)methylpiperidine;
1-[3-(5-(1,2,4-triazol-4-yl)-1H-indol-3-yl)propyl]-4-(4-methyl-2-phenylpiperazin-1-yl)piperidine;
1-[3-(5-(1,2,4-triazol-4-yl)-1H-indol-3-yl)propyl]-4-(benzimidazol-2-on-1-yl)piperidine:
1-[3-(5-(1,2,4-triazol-4-yl)-1H-indol-3-yl)propyl]-4-[6-(4-fluorophenyl)-4-methyl-3-oxopiperazin-1-yl]piperidine;
1-[3-(5-(1,2,4-triazol-4-yl)-1H-indol-3-yl)propyl]-4-[2-(4-fluorophenyl)-4-methylpiperazin-1-yl]piperidine;
1-[2-(5-(1,2,4-triazol-1-ylmethyl)-1H-indol-3-yl)ethyl]-3(R)-(3(R)-phenylmorpholin-4-ylmethyl)pyrrolidine;
and salts and prodrugs thereof.

7. A pharmaceutical composition comprising a compound of formula I as defined in claim 1 or a pharmaceutically acceptable salt thereof or a prodrug thereof in association with a pharmaceutically acceptable carrier.

8. A method for the treatment of migraine and associated conditions, cluster headache, chronic paroxysmal hemicrania, headache associated with vascular disorders, tension headache, and pediatric migraine, which method comprises administering to a patient in need of such treatment an effective amount of a compound of formula I as defined in claim 1, or a pharmaceutically acceptable salt thereof or a prodrug thereof.

* * * * *